(12) United States Patent
Liao et al.

(10) Patent No.: US 10,774,824 B2
(45) Date of Patent: Sep. 15, 2020

(54) MINIATURE FLUID CONTROL DEVICE

(71) Applicant: Microjet Technology Co., Ltd., Hsinchu (TW)

(72) Inventors: Hung-Hsin Liao, Hsinchu (TW); Shih-Chang Chen, Hsinchu (TW); Jia-Yu Liao, Hsinchu (TW); Yung-Lung Han, Hsinchu (TW); Chi-Feng Huang, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 352 days.

(21) Appl. No.: 15/861,818

(22) Filed: Jan. 4, 2018

(65) Prior Publication Data

US 2018/0187669 A1    Jul. 5, 2018

(30) Foreign Application Priority Data

Jan. 5, 2017    (TW) .............................. 106100266 A

(51) Int. Cl.
*F04B 43/04* (2006.01)
*F04B 45/047* (2006.01)
(Continued)

(52) U.S. Cl.
CPC .......... *F04B 43/046* (2013.01); *F04B 43/043* (2013.01); *F04B 43/095* (2013.01);
(Continued)

(58) Field of Classification Search
CPC .... F04B 43/043; F04B 43/046; F04B 43/095; F04B 45/047; F04B 17/003; F16K 99/0015; F16K 99/0048; F16K 2099/0094
See application file for complete search history.

(56) References Cited

U.S. PATENT DOCUMENTS 9,611,743 B2 *   4/2017   Toellner ................. A61M 1/101
9,989,047 B2 *   6/2018   Chen ..................... F04B 45/047
(Continued)

FOREIGN PATENT DOCUMENTS

CN    205383064 U    7/2016
EP     2998582 A1    3/2016
(Continued)

OTHER PUBLICATIONS

Extended European Search Report for Application No. 18150274.1, dated Mar. 27, 2018.

*Primary Examiner* — Peter J Bertheaud
(74) *Attorney, Agent, or Firm* — Birch, Stewart, Kolasch & Birch, LLP

(57) ABSTRACT

A miniature fluid control device for transporting gas is disclosed, which includes a gas inlet plate, a resonance plate, a piezoelectric actuator and a gas collecting plate stacked on each other. The gas inlet plate includes at least one inlet, at least one convergence channel and a circular cavity which forms a convergence chamber. The resonance plate has a central aperture. The piezoelectric actuator includes a suspension plate, an outer frame and a piezoelectric plate, wherein the suspension plate has a cylindrical bulge aligned with the circular cavity. The ratio of a second diameter of the cylindrical bulge to a first diameter of the circular cavity is set in a specified range to optimize the gas pressure of the transported gas, thus assuring efficiency of gas transmission of the miniature fluid control device.

16 Claims, 11 Drawing Sheets

(51) Int. Cl.
*F16K 99/00* (2006.01)
*F04B 43/09* (2006.01)

(52) U.S. Cl.
CPC ........ *F04B 45/047* (2013.01); *F16K 99/0015* (2013.01); *F16K 99/0048* (2013.01); *A61M 2205/0294* (2013.01); *F04B 2205/02* (2013.01); *F04B 2205/04* (2013.01); *F16K 2099/0094* (2013.01)

(56) References Cited

U.S. PATENT DOCUMENTS

| | | | |
|---|---|---|---|
| 10,451,051 B2 * | 10/2019 | Chen | F16K 99/0015 |
| 10,487,820 B2 * | 11/2019 | Chen | F04B 39/1066 |
| 2014/0377099 A1 * | 12/2014 | Hsueh | F04B 43/046 |
| | | | 417/413.2 |
| 2016/0076530 A1 * | 3/2016 | Chen | F04B 45/047 |
| | | | 417/413.2 |
| 2017/0218936 A1 * | 8/2017 | Chen | F04B 43/046 |

FOREIGN PATENT DOCUMENTS

| | | |
|---|---|---|
| EP | 3203072 A1 | 8/2017 |
| TW | 200422510 A | 11/2004 |
| TW | M490850 U | 12/2014 |
| TW | M512864 U | 11/2015 |
| TW | 205744376 U | 11/2016 |
| WO | WO 2016/175185 A1 | 11/2016 |

\* cited by examiner

MINIATURE FLUID CONTROL DEVICE

FIELD OF THE INVENTION

The present invention relates to a fluid control device, and more particularly to a miniature fluid control device for use with a slim and silent miniature pneumatic device.

BACKGROUND OF THE INVENTION

With the advancement of science and technology, fluid transportation devices used in many sectors such as pharmaceutical industries, computer techniques, printing industries or energy industries are developed toward elaboration and miniaturization. The fluid transportation devices are important components that are used in for example micro pumps, micro atomizers, printheads or industrial printers. Therefore, it is important to provide an improved structure of the fluid transportation device.

For example, in the pharmaceutical industries, pneumatic devices or pneumatic machines use motors or pressure valves to transfer gases. However, due to the volume limitations of the motors and the pressure valves, the pneumatic devices or the pneumatic machines are bulky in volume. In other words, the conventional pneumatic device fails to meet the miniaturization requirement, and it not suitable to be installed in or cooperated with a portable equipment. Moreover, during operations of the motor or the pressure valve, annoying noise is readily generated.

Therefore, there is a need of providing a miniature fluid control device with small, miniature, silent, portable and comfortable benefits and capable of stabilizing the pressure of the transferred gas in order to eliminate the above drawbacks.

SUMMARY OF THE INVENTION

The present invention provides a miniature fluid control device for use with a portable or wearable equipment or machine. The miniature fluid control device is capable of transporting gas. The miniature control device may comprise a gas inlet plate, a resonance plate and a piezoelectric actuator, wherein the gas inlet plate has a circular cavity for defining a convergence chamber, and the piezoelectric actuator comprises a suspension plate with a cylindrical bulge. The circular cavity of the gas inlet plate and the cylindrical bulge of the suspension plate are aligned with each other along a vertical direction, and the diameters of the circular cavity and the cylindrical bulge are in a specified ratio, thus preventing backflow occurring in the convergence chamber. Therefore, the gas pressure of the gas transported by the miniature fluid control device is optimized, and the working efficiency of the miniature fluid control device is improved.

In accordance with an aspect of the present invention, a miniature fluid control device is provided. The miniature fluid control device includes a gas inlet plate, a resonance plate and a piezoelectric actuator. The gas inlet plate includes a feeding surface and a coupling surface. At least one inlet is formed in the feeding surface. At least one convergence channel and a circular cavity are concavely formed in the coupling surface. The circular cavity has a first diameter. A first end of the convergence channel is in communication with the circular cavity. A second end of the convergence channel is in communication with the at least one inlet. A convergence chamber is defined by the circular cavity. After a gas is introduced into the at least one convergence channel through the at least one inlet, the gas is guided by the at least one convergence channel and converged to the convergence chamber. The resonance plate has a central aperture corresponding to the circular cavity of the gas inlet plate. The piezoelectric actuator includes a suspension plate, an outer frame, at least one bracket and a piezoelectric plate. The suspension plate has a first surface and an opposing second surface. A cylindrical bulge is formed on the second surface of the suspension plate. The cylindrical bulge and the circular cavity are aligned with each other along a vertical direction. The cylindrical bulge has a second diameter. There is a specified ratio of the second diameter to the first diameter so as to optimize the gas pressure of the transported gas. The outer frame is arranged around the suspension plate. The suspension plate and the outer frame are connected with each other through the at least one bracket. The piezoelectric plate is attached on the first surface of the suspension plate. The gas inlet plate, the resonance plate and the piezoelectric actuator are stacked on each other sequentially. A gap is formed between the resonance plate and the piezoelectric actuator to define a first chamber. After the gas is fed into the at least one inlet of the gas inlet plate, the gas is converged to the circular cavity through the at least one convergence channel, transferred through the central aperture of the resonance plate, introduced into the first chamber, transferred downwardly through a vacant space between the at least one bracket of the piezoelectric actuator, and exited from the miniature fluid control device. During the operation of the miniature fluid control device, the piezoelectric actuator makes the gas fed into the device and repeat above-mentioned actions, so that the miniature fluid control device continuously outputs the transported gas. Since the ratio of the second diameter to the first diameter is set in a specified range, the gas pressure of the transported gas is optimized and the efficiency of gas transmission is assured.

The above contents of the present invention will become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

The present invention provides a miniature fluid control device for use with a miniature pneumatic device. The miniature fluid control device is capable of transporting gas. The miniature pneumatic device may be used in many sectors such as pharmaceutical industries, energy industries, computer techniques or printing industries for transporting gases.

Figure 1A:
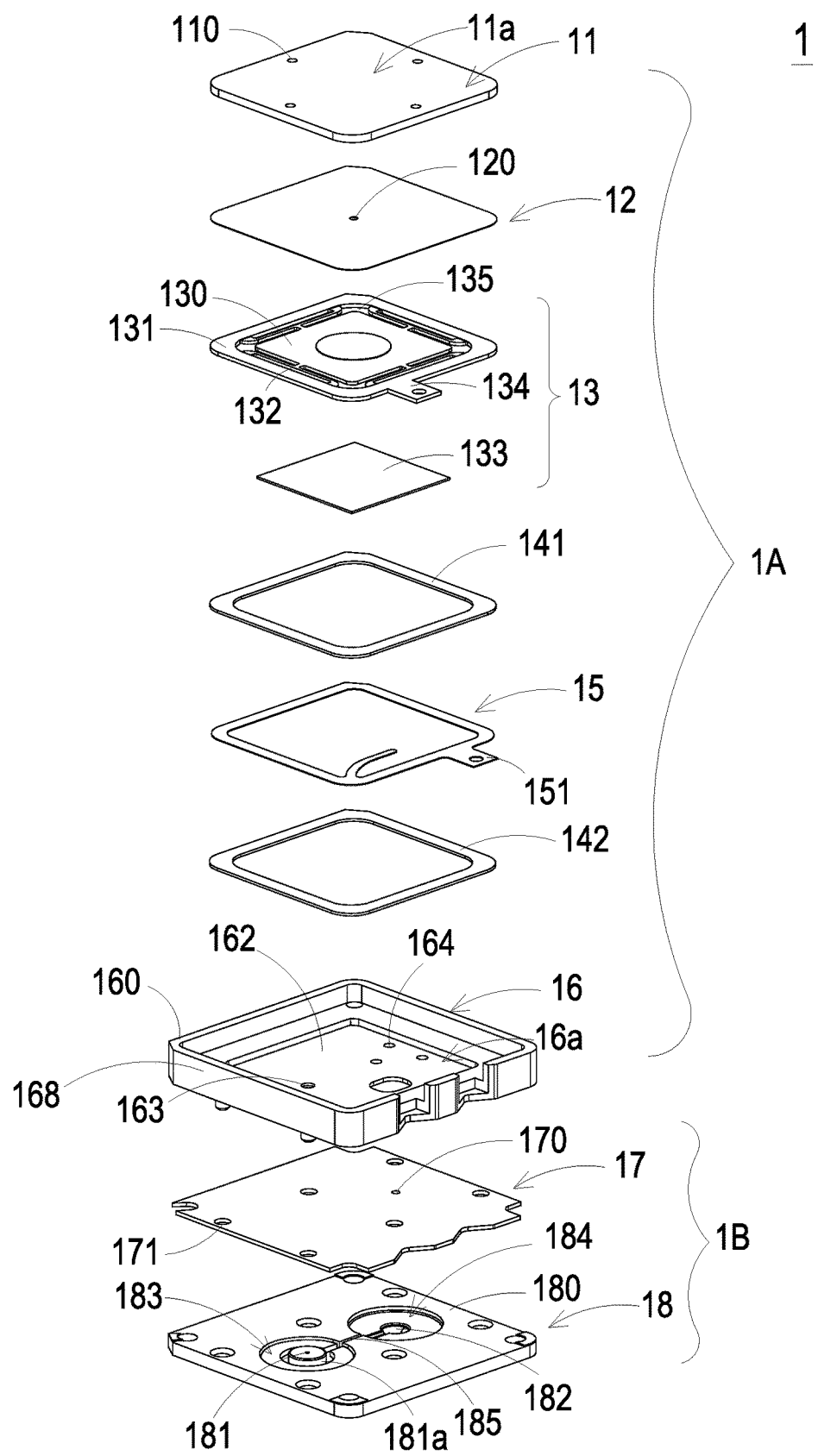
FIG. 1A is a schematic exploded view illustrating a miniature pneumatic device according to an embodiment of the present invention and taken along a front side.
Figure 1B:
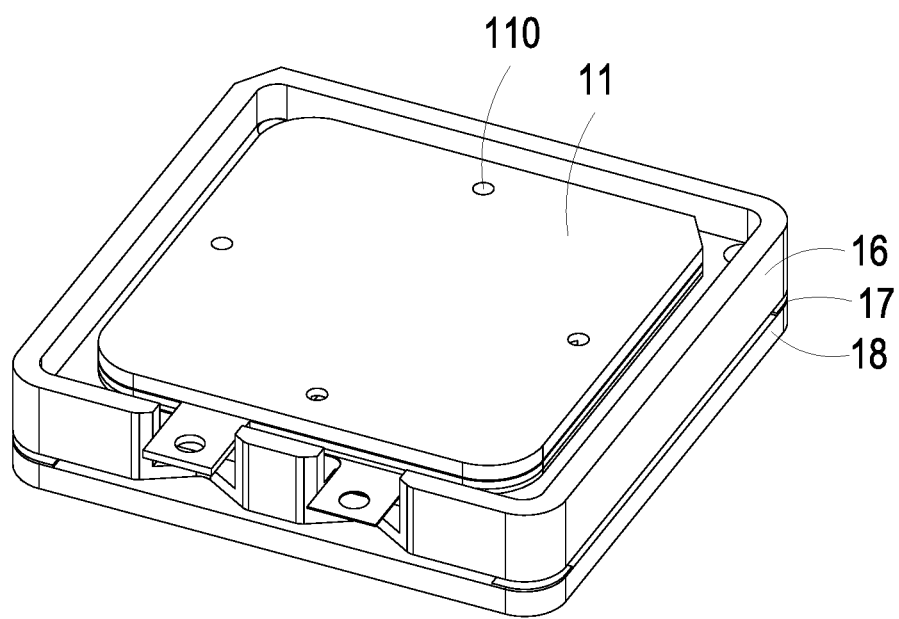
FIG. 1B is a schematic assembled view illustrating the miniature pneumatic device of FIG. 1A.
Figure 2A:
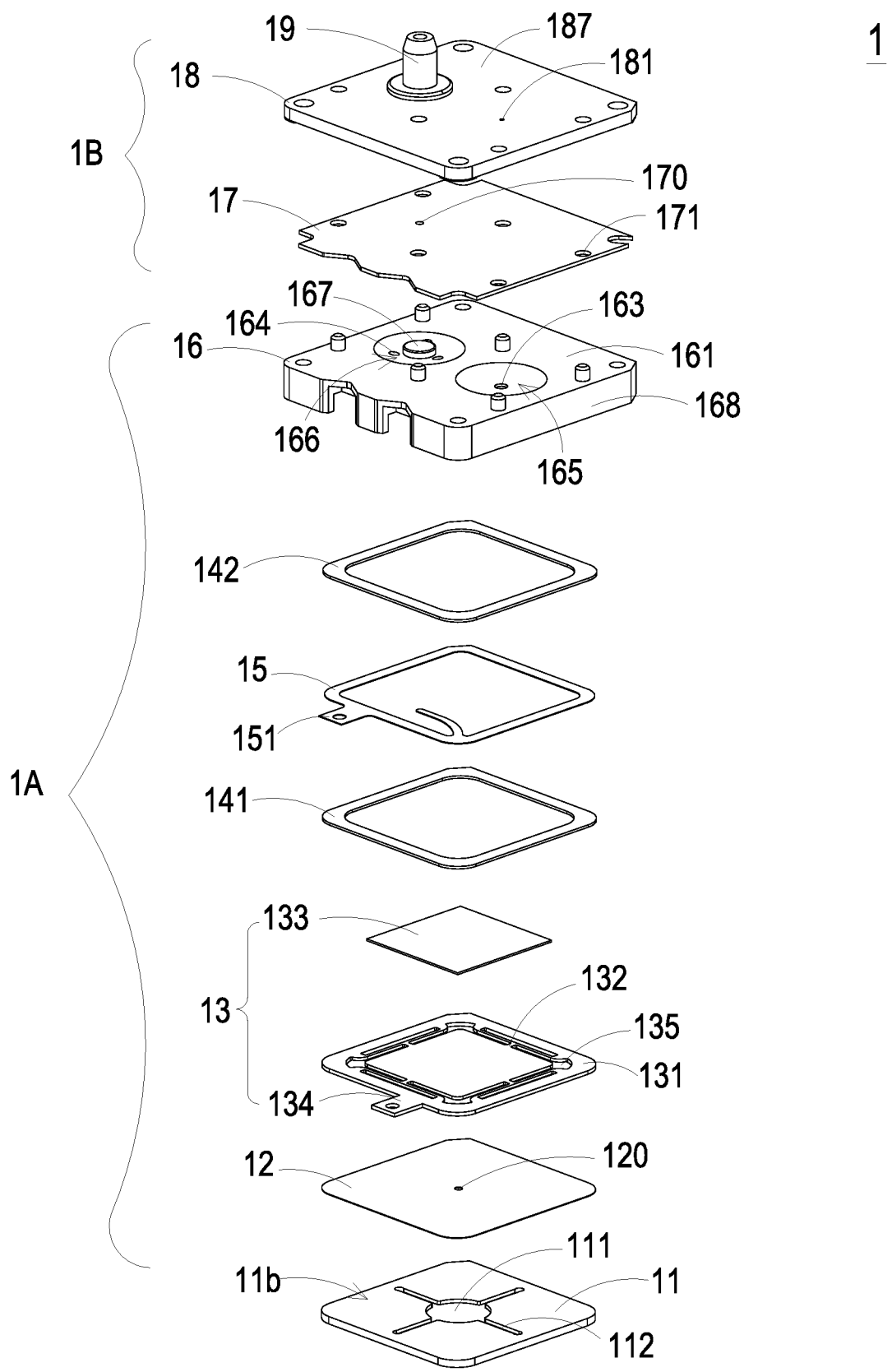
FIG. 2A is a schematic exploded view illustrating the miniature pneumatic device according to the embodiment of the present invention and taken along a rear side.
Figure 2B:
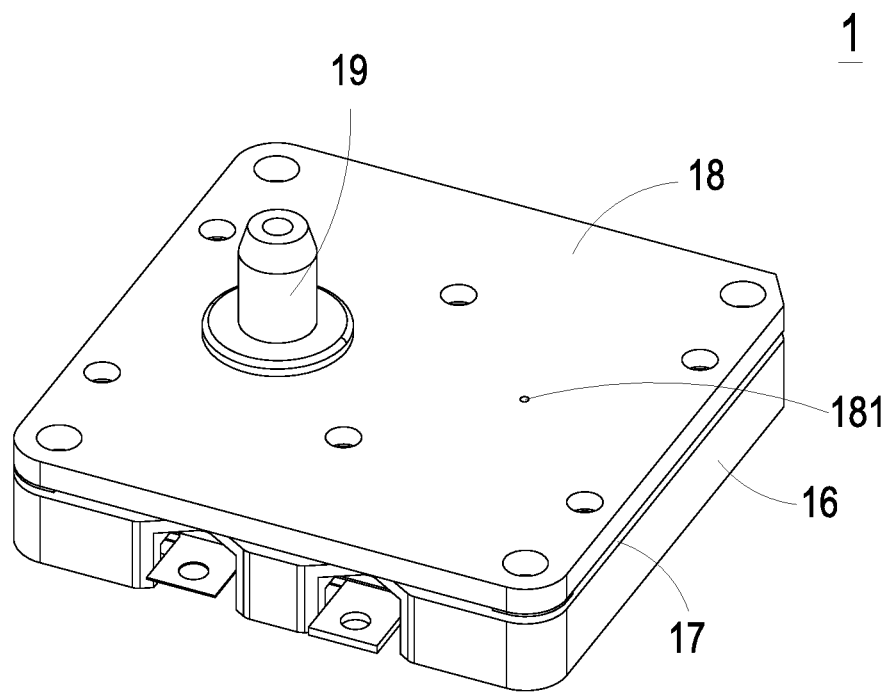
FIG. 2B is a schematic assembled view illustrating the miniature pneumatic device of FIG. 2A.

Please refer to FIGS. 1A, 1B, 2A and 2B. FIG. 1A is a schematic exploded view illustrating a miniature pneumatic device according to an embodiment of the present invention and taken along a front side. FIG. 1B is a schematic assembled view illustrating the miniature pneumatic device of FIG. 1A. FIG. 2A is a schematic exploded view illustrating the miniature pneumatic device according to the embodiment of the present invention and taken along a rear side. FIG. 2B is a schematic assembled view illustrating the miniature pneumatic device of FIG. 2A.

As shown in FIGS. 1A, 1B, 2A and 2B, the miniature pneumatic device 1 comprises a miniature fluid control device 1A and a miniature valve device 1B. In this embodiment, the miniature fluid control device 1A comprises a gas inlet plate 11, a resonance plate 12, a piezoelectric actuator 13, a first insulation plate 141, a conducting plate 15, a second insulation plate 142 and gas-collecting plate 16. The piezoelectric actuator 13 is aligned with the resonance plate 12. The gas inlet plate 11, the resonance plate 12, the piezoelectric actuator 13, the first insulation plate 141, the conducting plate 15, the second insulation plate 142 and the gas collecting plate 16 are stacked on each other sequentially to be assembled while an outward surface of the gas inlet plate 11 is towards an input side. Moreover, the piezoelectric actuator 13 comprises a suspension plate 130, an outer frame 131, at least one bracket 132 and a piezoelectric plate 133. In this embodiment, the miniature valve device 1B comprises a valve film 17 and a gas outlet plate 18.

As shown in FIG. 1A, the gas collecting plate 16 comprises a bottom plate and a sidewall 168 protruding from the edges of the bottom plate. The bottom plate and the sidewall 168 collaboratively define an accommodation space 16a where the piezoelectric actuator 13 is disposed within. The structure of the miniature pneumatic device 1 in assembled state, taken from the front side, is shown in FIG. 1B and FIGS. 6A to 6E. As the miniature fluid control device 1A and the miniature valve device 1B are combined together, the valve film 17 and the gas outlet plate 18 of the miniature valve device 1B are stacked on each other and positioned on the bottom side of the gas collecting plate 16 of the miniature fluid control device 1A. The gas outlet plate 18 has a pressure-releasing perforation 181 and an outlet structure 19. The outlet structure 19 is adapted to be in communication with an inner space inside a target equipment (not shown), and the pressure-releasing perforation 181 is adapted to discharge the gas inside the miniature valve device 1B. As so, the gas pressure of the inner space of the target equipment can be released.

The miniature pneumatic device 1 in assembled state allows a gas to be fed into the miniature fluid control device 1A through at least one inlet 110 of the gas inlet plate 11 from the input side. The piezoelectric actuator 13 is operable to be activated, and in response of the actions of the piezoelectric actuator 13, the gas is transferred downwardly through plural pressure chambers to the miniature valve device 1B. In the miniature valve device 1B, the gas is transferred in one direction, being discharged from the outlet structure 19 and flows into the inner space of the target equipment (not shown). As a result, the pressure of the gas in the inner space of the target equipment is accumulated.

Please refer to FIGS. 1A and 2A again. The gas inlet plate 11 of the miniature fluid control device 1A comprises a feeding surface 11a, a coupling surface 11b opposing to the feeding surface 11a, and at least one inlet 110 which is formed in the feeding surface 11a. In this embodiment, the gas inlet plate 11 has four inlets 110. The inlets 110 run through the feeding surface 11a and the coupling surface 11b of the gas inlet plate 11, and the feeding surface 11a is toward exterior of the miniature pneumatic device 1, where is defined as the input side. In response to the action of the atmospheric pressure, the gas is introduced into the miniature fluid control device 1A through the inlets 110. As shown in FIG. 2A, a circular cavity 111 and at least one convergence channel 112 are concavely formed on the coupling surface 11b of the gas inlet plate 11. A first end of the at least one convergence channel 112 is in communication with the circular cavity 111 of the gas inlet plate 11, while a second end of the at least one convergence channel 112 is in communication with the at least one inlet 110 of the gas inlet plate 11. The number of the at least one convergence channel 112 is identical to the number of the at least one inlet 110. In this embodiment, the gas inlet plate 11 has four convergence channels 112. It is noted that the number of the at least one convergence channel 112 and the number of the at least one inlet 110 may be varied according to the practical requirements.

Moreover, the circular cavity 111 is formed on the central of the coupling surface 11b of the gas inlet plate 11 and located at the intersection of the four convergence channels 112 that forming a convergence chamber for temporarily storing the gas. The circular cavity 111 is in communication with all of the convergence channels 112, such that the gas entered by the inlets 110 would be introduced into the at least one convergence channel 112 and is guided to the circular cavity 111. In this embodiment, the at least one inlet 110, the at least one convergence channel 112 and the circular cavity 111 of the gas inlet plate 11 are integrally formed.

Preferably but not exclusively, the gas inlet plate 11 is made of stainless steel. Moreover, the depth of the convergence chamber defined by the circular cavity 111, is equal to the depth of the at least one convergence channel 112, both of which are preferably in the range between 0.2 mm and 0.4 mm. The resonance plate 12 is made of flexible material, which is preferably but not exclusively copper. The resonance plate 12 further has a central aperture 120 corresponding to the circular cavity 111 of the gas inlet plate 11 that providing the gas for flowing through.

Figure 3A:
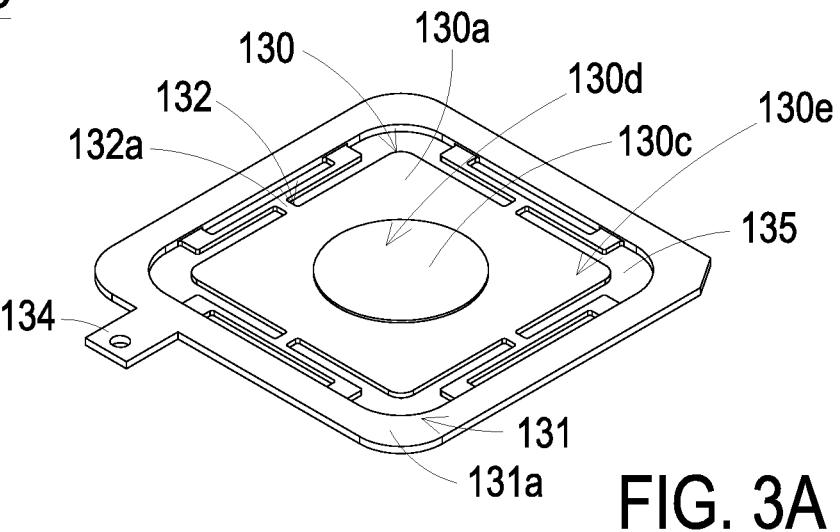
FIG. 3A is a schematic perspective view illustrating the piezoelectric actuator of the miniature pneumatic device of FIG. 1A and taken along the front side.
Figure 3B:
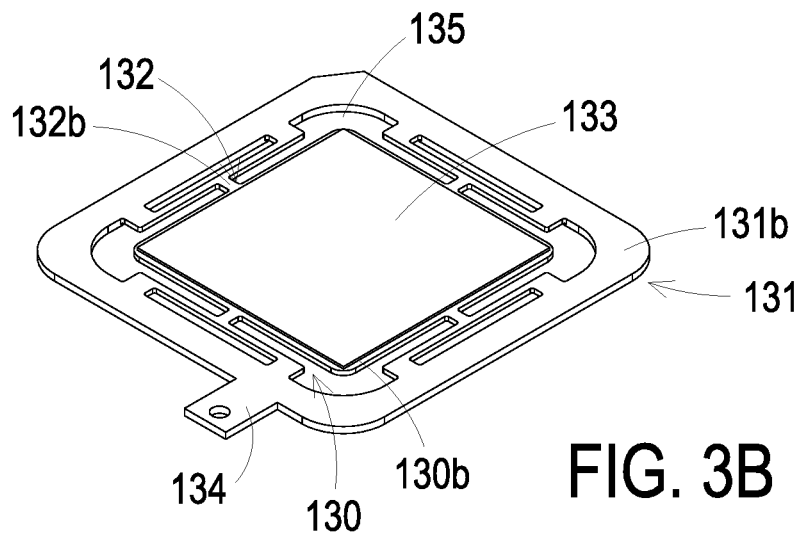
FIG. 3B is a schematic perspective view illustrating the piezoelectric actuator of the miniature pneumatic device of FIG. 1A and taken along the rear side.
Figure 3C:
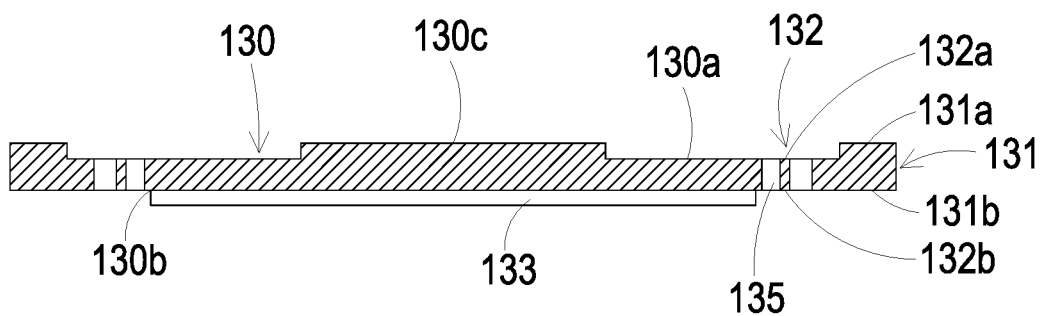
FIG. 3C is a schematic cross-sectional view illustrating the piezoelectric actuator of the miniature pneumatic device of FIG. 1A.

FIG. 3A is a schematic perspective view illustrating the piezoelectric actuator of the miniature pneumatic device of FIG. 1A and taken along the front side. FIG. 3B is a schematic perspective view illustrating the piezoelectric actuator of the miniature pneumatic device of FIG. 1A and taken along the rear side. FIG. 3C is a schematic cross-sectional view illustrating the piezoelectric actuator of the miniature pneumatic device of FIG. 1A. As shown in FIGS. 3A, 3B and 3C, the piezoelectric actuator 13 comprises the suspension plate 130, the outer frame 131, the at least one bracket 132, and the piezoelectric plate 133. The piezoelectric plate 133 is attached on a first surface 130b of the suspension plate 130. In response to an applied voltage, the piezoelectric plate 133 would be subjected to a curvy vibration. The suspension plate 130 comprises a middle portion 130d and a periphery portion 130e. When the piezoelectric plate 133 is subjected to the curvy vibration, the suspension plate 130 is also subjected to the curvy vibration and vibrates from the middle portion 130d to the periphery portion 130e. The at least one bracket 132 is connected between the suspension plate 130 and the outer frame 131, while the two ends of the bracket 132 are connected with the outer frame 131 and the suspension plate 130 respectively that the bracket 131 can elastically support the suspension plate 130. At least one vacant space 135 is formed between the bracket 132, the suspension plate 130 and the outer frame 131 for allowing the gas to go through. The type of the suspension plate 130 and the outer frame 131, and the type and the number of the at least one bracket 132 may be varied according to the practical requirements. Moreover, a conducting pin 134 is protruding outwardly from the outer frame 131 so as to be electrically connected with an external circuit (not shown).

The suspension plate 130 has a cylindrical bulge 130c that makes the suspension plate 130 a stepped structure. The cylindrical bulge 130c is formed on a second surface 130a of the suspension plate 130, wherein the second surface 130a is opposing to the first surface 130b. The thickness of cylindrical bulge 130c is in the range between 0.02 mm and 0.08 mm, and preferably 0.03 mm. As shown in FIGS. 3A and 3C, a top surface of the cylindrical bulge 130c of the suspension plate 130 is coplanar with a second surface 131a of the outer frame 131, while the second surface 130a of the suspension plate 130 is coplanar with a second surface 132a of the bracket 132. Moreover, there is a drop of specified amount from the cylindrical bulge 130c of the suspension plate 130 (or the second surface 131a of the outer frame 131) to the second surface 130a of the suspension plate 130 (or the second surface 132a of the bracket 132). As shown in FIGS. 3B and 3C, a first surface 130b of the suspension plate 130, a first surface 131b of the outer frame 131 and a first surface 132b of the bracket 132 are coplanar with each other. The piezoelectric plate 133 is attached on the first surface 130b of the suspension plate 130. In this embodiment, the suspension plate 130, the at least bracket 132 and the outer frame 131 are integrally formed and produced by using a metal plate (e.g., a stainless steel plate). Moreover, the length of the suspension plate 130 is in the range between 8 mm and 9 mm.

The piezoelectric plate 133 has the same shape with the suspension plate 130 but in smaller size, which means the longest side of the piezoelectric plate 133 is equal to or shorter than the longest side of the suspension plate 130. For example, the length of a side of the piezoelectric plate 133 is in the range between 7.5 mm and 8.5 mm.

In some embodiments, the length of the suspension plate 130 is 7.5 mm, and the length of the piezoelectric plate 133 is 7 mm, which is slightly smaller than the length of the suspension plate 130.

Figure 4A:
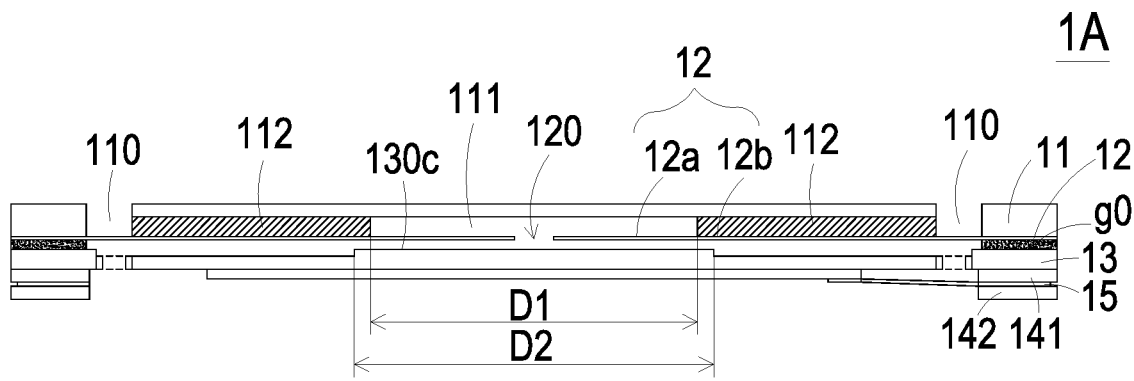
FIGS. 4A to 4E schematically illustrate the actions of the miniature fluid control device of the miniature pneumatic device of FIG. 1A.

FIGS. 4A to 4E schematically illustrate the actions of the miniature fluid control device of the miniature pneumatic device of FIG. 1A. As shown in FIG. 4A, the cylindrical bulge 130c of the suspension plate 130 and the circular cavity 111 of the gas inlet plate 11 are aligned with each other along the vertical direction. The circular cavity 111 has a first diameter D1. The cylindrical bulge 130c has a second diameter D2. In case that the first diameter D1 is fixed (e.g., 4 mm) and the second diameter D2 is changed, the relationship between the ratio of D2 to D1 and the working characteristic value (e.g., gas pressure) is listed in Table 1.

TABLE 1

| First diameter D1 (mm) | 4 | | | | | | | |
|---|---|---|---|---|---|---|---|---|
| Second diameter D2 (mm) | 3.4 | 3.6 | 3.8 | 4.0 | 4.4 | 4.6 | 4.8 | 5.0 |
| D2/D1 | 0.85 | 0.9 | 0.95 | 1.0 | 1.1 | 1.15 | 1.2 | 1.25 |
| Gas pressure (mmHg) | 335 | 375 | 413 | 415 | 410 | 384 | 317 | 293 |

From the results of Table 1, it is found that the ratio D2/D1 (i.e., the ratio of the second diameter D2 to the first diameter D1) has a high influence on the flow rate of the gas transported by the miniature fluid control device 1A. In case that the ratio D2/D1 is in the range between 0.95 and 1.15, the efficiency of gas transmission is optimized, as the gas pressure of the gas transported by the miniature fluid control device 1A is at more than 380 mmHg. More especially, in case that the ratio D2/D1 is in the range between 1 and 1.1, the gas pressure of the gas transported by the miniature fluid control device 1A is at more than 410 mmHg. In other words, the ratio D2/D1 affects the working characteristic value (e.g., gas pressure) of the miniature fluid control device 1A. Since the present invention provides the miniature fluid control device 1A with a specified ratio D2/D1, which is preferably in the range between 0.95 and 1.15, the gas pressure of the gas transported by the miniature fluid control device 1A is in an optimum range that assuring the efficiency of gas transmission. It is speculated that the reason that the ratio D2/D1 has significant influence on the gas pressure of the gas transported by the miniature fluid control device 1A is that gas backflow occurring in the convergence chamber is prevented. The relationship between the ratio D2/D1 and the working characteristic value is realized according to the results of experiments rather than theoretical mathematic formulae.

Preferably, the suspension plate 130 of the piezoelectric actuator 13 used in the miniature pneumatic device 1 of the present invention is a square suspension plate. In comparison with the circular suspension plate, the square suspension plate is more power-saving. The comparison between the consumed power and the operating frequency for the suspension plates of different types and sizes is shown in Table 2.

TABLE 2

| Type and size of suspension plate | Operating frequency | Consumed power |
| --- | --- | --- |
| Square (side length: 10 mm) | 18 kHz | 1.1 W |
| Circular (diameter: 10 mm) | 28 kHz | 1.5 W |
| Square (side length: 9 mm) | 22 kHz | 1.3 W |
| Circular (diameter: 9 mm) | 34 kHz | 2 W |
| Square (side length: 8 mm) | 27 kHz | 1.5 W |
| Circular (diameter: 8 mm) | 42 kHz | 2.5 W |

From the results of Table 2, it is found that the piezoelectric actuator with the square suspension plate is more power-saving than the piezoelectric actuator with the circular suspension plate of same size. That is, the piezoelectric actuator with the square suspension plate consumes less power. It is generally known that the consumed power of the capacitive load at the resonance frequency is positively related to the resonance frequency. Since the resonance frequency of the square suspension plate is obviously lower than that of the circular square suspension plate of same size, the consumed power of the square suspension plate is lower. Taking advantage of the power-saving square suspension plate, the miniature pneumatic device 1 would be suitably used in the wearable device. The fact that the square suspension plate is more power-saving than the circular suspension plate is realized according to the results of experiments rather than theoretical mathematic formulae.

Please refer to FIGS. 1A and 2A again. The miniature fluid control device 1A further comprises the first insulation plate 141, the conducting plate 15 and the second insulation plate 142. The first insulation plate 141, the conducting plate 15 and the second insulation plate 142 are stacked on each other sequentially and located under the piezoelectric actuator 13. The profiles of the first insulation plate 141, the conducting plate 15 and the second insulation plate 142 substantially match the profile of the outer frame 131 of the piezoelectric actuator 13. The first insulation plate 141 and the second insulation plate 142 are made of an insulating material (e.g. a plastic material) for providing insulating efficacy. The conducting plate 15 is made of an electrically conductive material (e.g. a metallic material) for providing electrically conducting efficacy. Moreover, the conducting plate 15 has a conducting pin 151 so as to be electrically connected with an external circuit (not shown).

FIGS. 4A to 4E schematically illustrate the actions of the miniature fluid control device of the miniature pneumatic device of FIG. 1A. As shown in FIG. 4A, the gas inlet plate 11, the resonance plate 12, the piezoelectric actuator 13, the first insulation plate 141, the conducting plate 15 and the second insulation plate 142 of the miniature fluid control device 1A are stacked on each other sequentially. Moreover, there is a gap g0 between the resonance plate 12 and the outer frame 131 of the piezoelectric actuator 13, which is formed and maintained by a filler (e.g. a conductive adhesive) inserted therein in this embodiment. The gap g0 ensures the proper distance between the resonance plate 12 and the cylindrical bulge 130c of the suspension plate 130, so that the contact interference is reduced and the generated noise is largely reduced.

Please refer to FIGS. 4A to 4E again. A convergence chamber is defined by the resonance plate 12 and the circular cavity 111 of the gas inlet plate 11 collaboratively for converging the gas. A first chamber 121 is formed between the resonance plate 12 and the piezoelectric actuator 13, and is in communication with the convergence chamber through the central aperture 120 of the resonance plate 12. Meanwhile, the peripheral regions of the first chamber 121 are in communication with the underlying miniature valve device 1B through the vacant spaces 135 of the piezoelectric actuator 13

Figure 4B:
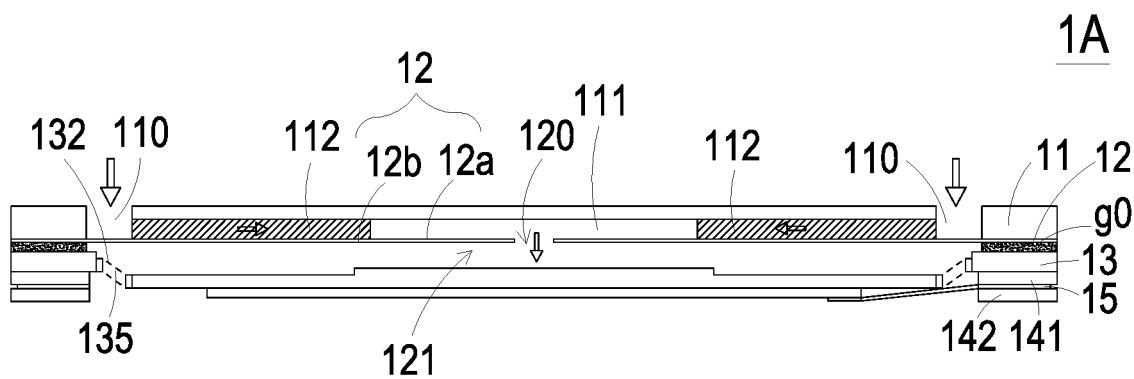

Please refer to FIG. 4B. When the miniature fluid control device 1A of the miniature pneumatic device 1 is enabled, the piezoelectric actuator 13 is actuated in response to an applied voltage. Consequently, the piezoelectric actuator 13 vibrates along a vertical direction in a reciprocating manner, while the brackets 132 are served as the fulcrums. The resonance plate 12 except for the part of it fixed on the gas inlet plate 11 is hereinafter referred as a movable part 12a, while the rest is referred as a fixed part 12b. Since the resonance plate 12 is light and thin, the movable part 12a vibrates along with the piezoelectric actuator 13 because of the resonance of the piezoelectric actuator 13. In other words, the movable part 12a is reciprocated and subjected to a curvy deformation.

Figure 4C:
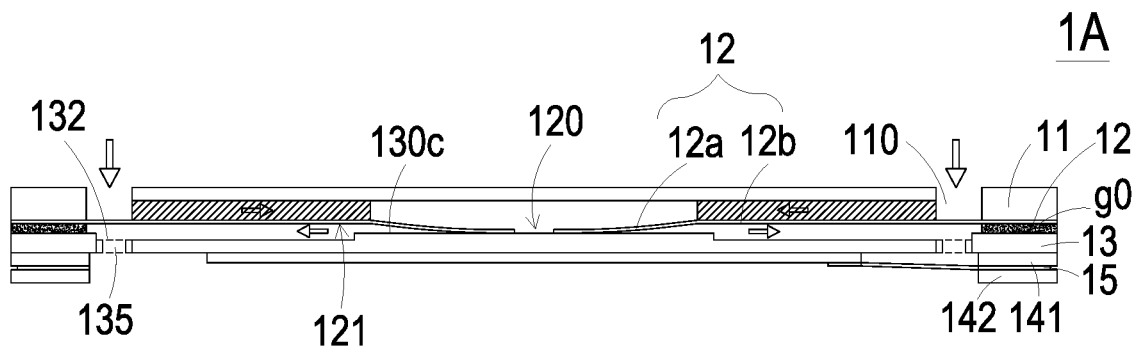

As shown in FIG. 4C, during the vibration of the movable part 12a of the resonance plate 12, the movable part 12a moves down till being contacted with the cylindrical bulge 130c of the suspension plate 130. In the meantime, the volume of the first chamber 121 is shrunken and a middle space which was communicating with the convergence chamber is closed. As a result, the pressure gradient occurs to push the gas in the first chamber 121 moving toward peripheral regions of the first chamber 121 and flowing downwardly through the vacant spaces 135 of the piezoelectric actuator 13.

Figure 4D:
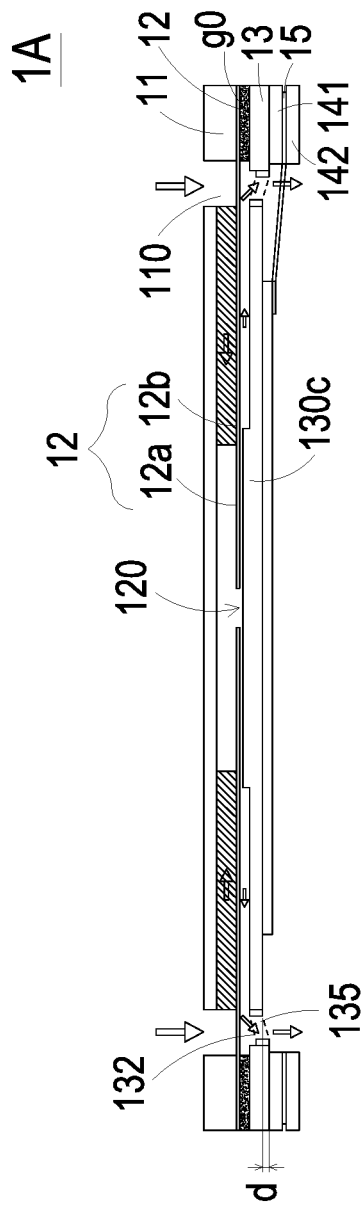

As shown in FIG. 4D, which illustrates consecutive action following the action in FIG. 4C. The movable part 12a has returned its original position when the piezoelectric actuator 13 has ascended at a vibration displacement d to an upward position. Consequently, the volume of the first chamber 121 is consecutively shrunken that generating the pressure gradient which makes the gas in the first chamber 121 continuously pushed toward peripheral regions and results in an exterior gas continuously fed into the inlets 110 of the gas inlet plate 11 and transferred to the central cavity 111.

Figure 4E:
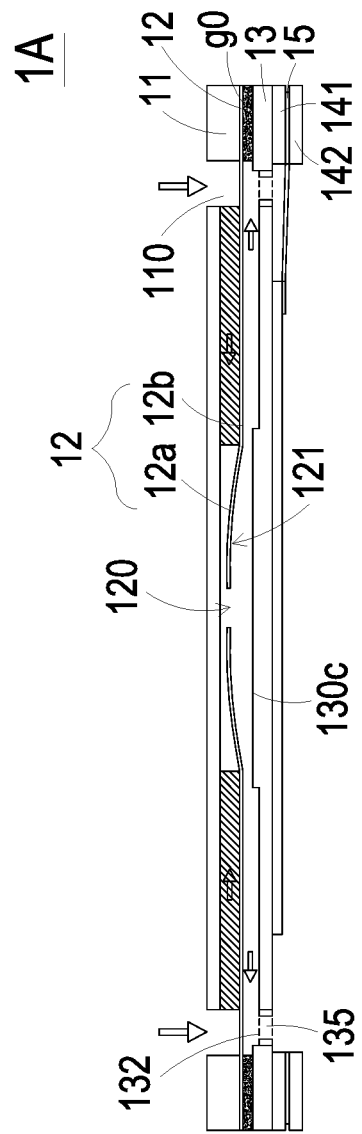

Then, as shown in FIG. 4E, the resonance plate 12 moves upwardly, which is caused by the resonance of the upward motion of the piezoelectric actuator 13. Under this circumstance, the volume of the first chamber 121 expends, which results in suction applied to the gas in the central cavity 111. The gas in the central cavity 111 is transferred to the first chamber 121 through the central aperture 120 of the resonance plate 12, then transferred downwardly through the vacant spaces 135 of the piezoelectric actuator 13, exiting from the miniature fluid control device 1A.

From the above discussions, when the resonance plate 12 is vibrated along the vertical direction in the reciprocating manner, the gap g0 between the resonance plate 12 and the piezoelectric actuator 13 is helpful to increase the amplitude of the resonance plate 12. That is, due to the gap g0 between the resonance plate 12 and the piezoelectric actuator 13, the amplitude of the resonance plate 12 is increased when the resonance occurs. Consequently, a pressure gradient is generated in the fluid channels of the miniature fluid control device 1A to facilitate the gas to flow at a high speed. Moreover, since there is an impedance difference between the feeding direction and the exiting direction, the gas can be transmitted from the inlet side to the outlet side. Moreover, even if the outlet side has a gas pressure, the miniature fluid control device 1A still has the capability of pushing out the gas while achieving the silent efficacy.

In some embodiments, the vibration frequency of the resonance plate 12 along the vertical direction in the reciprocating manner is identical to the vibration frequency of the piezoelectric actuator 13. That is, the resonance plate 12 and the piezoelectric actuator 13 are synchronously vibrated along the upward direction or the downward direction. It is noted that numerous modifications and alterations of the actions of the miniature fluid control device 1A may be made while retaining the teachings of the invention.

Figure 5A:
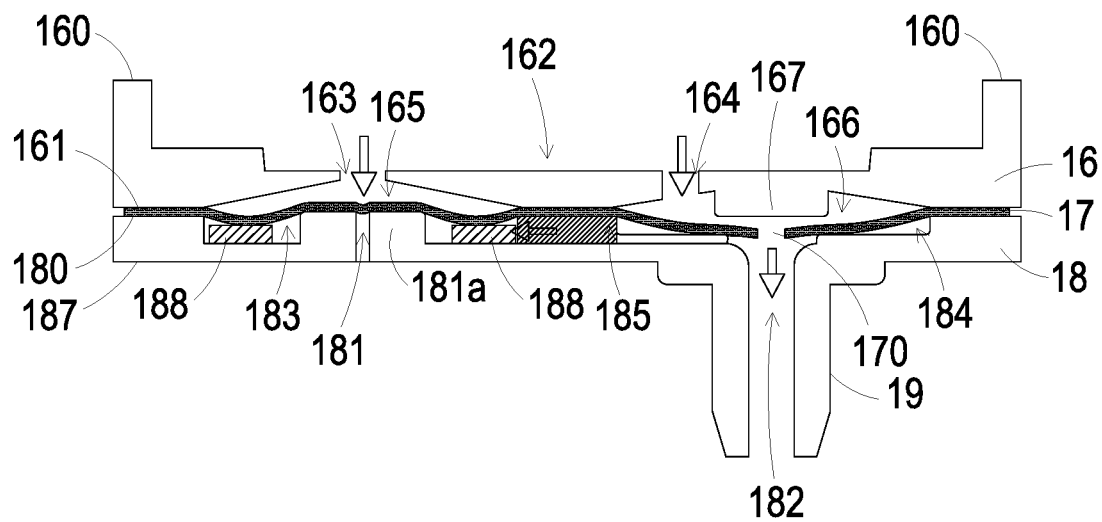
FIG. 5A schematically illustrate a gas-collecting operation of the gas collecting plate and miniature valve device of the miniature pneumatic device of FIG. 1A.
Figure 5B:
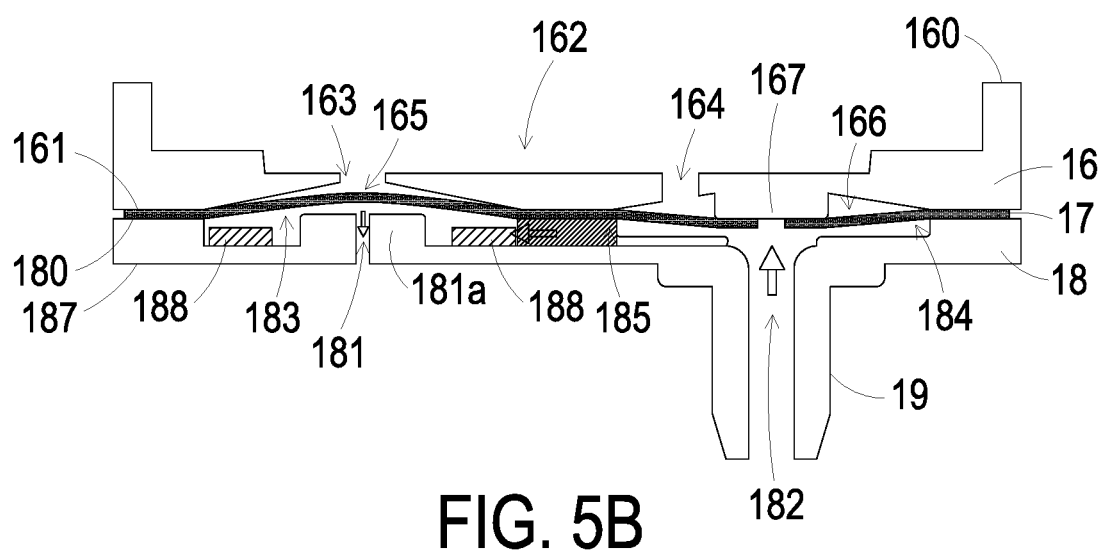
FIG. 5B schematically illustrate a gas-releasing operation of the gas collecting plate and miniature valve device of the miniature pneumatic device of FIG. 1A.

Please refer to FIGS. 1A, 2A, 5A and 5B. FIG. 5A schematically illustrate a gas-collecting operation of the gas collecting plate and miniature valve device of the miniature pneumatic device of FIG. 1A. FIG. 5B schematically illustrate a gas-releasing operation of the gas collecting plate and miniature valve device of the miniature pneumatic device of FIG. 1A. The valve film 17 and the gas outlet plate 18 of the miniature valve device 1B are stacked on each other sequentially. Moreover, the miniature valve device 1B cooperates with the gas collecting plate 16 of the miniature fluid control device 1A.

In this embodiment, the gas collecting plate 16 comprises a first surface 160 and a second surface 161 (also referred as a fiducial surface). The first surface 160 of the gas collecting plate 16 is concaved to define a gas-collecting chamber 162 which accommodates the piezoelectric actuator 13. The gas that is transferred downwardly by the miniature fluid control device 1A is temporarily accumulated in the gas-collecting chamber 162. The gas collecting plate 16 has a first perforation 163 and a second perforation 164. A first end of the first perforation 163 and a first end of the second perforation 164 are in communication with the gas-collecting chamber 162. A second end of the first perforation 163 and a second end of the second perforation 164 are respectively in communication with a first pressure-releasing chamber 165 and a first outlet chamber 166, which are formed on the second surface 161 of the gas collecting plate 16. Moreover, the gas collecting plate 16 has a raised structure 167 corresponding to the first outlet chamber 166. For example, the raised structure 167 includes but is not limited to a cylindrical post. The raised structure 167 is located at a level higher than the second surface 161 of the gas collecting plate 16.

The gas outlet plate 18 comprises a pressure-releasing perforation 181, an outlet perforation 182, a first surface 180 (also referred as a fiducial surface) and a second surface 187. The pressure-releasing perforation 181 and the outlet perforation 182 run through the first surface 180 and the second surface 187. The first surface 180 of the gas outlet plate 18 is concaved to define a second pressure-releasing chamber 183 and a second outlet chamber 184. The pressure-releasing perforation 181 is located at a center of the second pressure-releasing chamber 183. Moreover, the gas outlet plate 18 further comprises a communication channel 185 between the second pressure-releasing chamber 183 and the second outlet chamber 184 for allowing the gas to go through. A first end of the outlet perforation 182 is in communication with the second outlet chamber 184. A second end of the outlet perforation 182 is in communication with an outlet structure 19 to gain access to the inner space of the target equipment. The outlet structure 19 is in connected with the target equipment (not shown). The equipment is for example but not limited to a gas-pressure driving equipment.

The valve film 17 comprises a valve opening 170 and plural positioning openings 171 (see FIG. 1A).

After the gas collecting plate 16, the valve film 17 and the gas outlet plate 18 are combined together, the pressure-releasing perforation 181 of the gas outlet plate 18 is aligned with the first perforation 163 of the gas collecting plate 16, the second pressure-releasing chamber 183 of the gas outlet plate 18 is aligned with the first pressure-releasing chamber 165 of the gas collecting plate 16, and the second outlet chamber 184 of the gas outlet plate 18 is aligned with the first outlet chamber 166 of the gas collecting plate 16. The valve film 17 is arranged between the gas collecting plate 16 and the gas outlet plate 18 for blocking the communication between the first pressure-releasing chamber 165 and the second pressure-releasing chamber 183. The valve opening 170 of the valve film 17 is arranged between the second perforation 164 and the outlet perforation 182. Moreover, the valve opening 170 of the valve film 17 is aligned with the raised structure 167 corresponding to the first outlet chamber 166 of the gas collecting plate 16. Due to the arrangement of the single valve opening 170, the gas can be transferred through the miniature valve device 1B in one direction in response to the pressure difference.

In this embodiment, the gas outlet plate 18 has the convex structure 181*a* beside a first end of the pressure-releasing perforation 181. Preferably but not exclusively, the convex structure 181*a* is a cylindrical post. The top surface of the convex structure 181*a* is located at a level higher than the first surface 180 of the gas outlet plate 18. Consequently, the pressure-releasing perforation 181 can be quickly contacted with and closed by the valve film 17. Moreover, the convex structure 181*a* can provide a pre-force against the valve film 17 to achieve a good sealing effect. In this embodiment, the gas outlet plate 18 further comprises a position-limiting structure 188. The position-limiting structure 188 is disposed within the second pressure-releasing chamber 183. Preferably but not exclusively, the position-limiting structure 188 is a ring-shaped structure. While the gas-collecting operation of the miniature valve device 1B is performed, the position-limiting structure 188 can assist in supporting the valve film 17 and avoid collapse of the valve film 17. Consequently, the valve film 17 can be opened or closed more quickly.

Hereinafter, the gas-collecting operation of the miniature valve device 1B will be illustrated with reference to FIG. 5A. In case that the gas from the miniature fluid control device 1A is transferred downwardly to the miniature valve device 1B, or the ambient air pressure is higher than the gas pressure of the inner space of the target equipment which is in communication with the outlet structure 19, the gas will be transferred from the miniature fluid control device 1A to the gas-collecting chamber 162 of the gas collecting plate 16. Then, the gas is transferred downwardly to the first pressure-releasing chamber 165 and the first outlet chamber 166 through the first perforation 163 and the second perforation 164. In response to the downward gas, the flexible valve film 17 is subjected to a downward curvy deformation. Consequently, the volume of the first pressure-releasing chamber 165 is expanded, and the valve film 17 is in close contact with the first end of the pressure-releasing perforation 181 corresponding to the first perforation 163. Under this circumstance, the pressure-releasing perforation 181 of the gas outlet plate 18 is closed, and thus the gas within the second pressure-releasing chamber 183 is not leaked out from the pressure-releasing perforation 181. In this embodiment, the gas outlet plate 18 has the convex structure 181*a* beside of the first end of the pressure-releasing perforation 181. Due to the arrangement of the convex structure 181*a*, the pressure-releasing perforation 181 can be quickly closed by the valve film 17. Moreover, the convex structure 181*a* can provide a pre-force against the valve film 17 to achieve a good sealing effect. The position-limiting structure 188 is arranged around the pressure-releasing perforation 181 to assist in supporting the valve film 17 and avoid collapse of the valve film 17. On the other hand, the gas is transferred downwardly to the first outlet chamber 166 through the second perforation 164. In response to the downward gas, the valve film 17 corresponding to the first outlet chamber 166 is also subjected to the downward curvy deformation. Consequently, the valve opening 170 of the valve membrane 17 is correspondingly opened to the downward side. Under this circumstance, the gas is transferred from the first outlet chamber 166 to the second outlet chamber 184 through the valve opening 170. Then, the gas is transferred to the outlet structure 19 through the outlet perforation 182 and then transferred to the inner space of the target equipment which is in communication with the outlet structure 19. Consequently, the purpose of collecting the gas pressure is achieved.

Hereinafter, the gas-releasing operation of the miniature valve device 1B will be illustrated with reference to FIG. 5B. For performing the gas-releasing operation, the user may adjust the amount of the gas to be fed into the miniature fluid control device 1A, so that the gas is no longer transferred to the gas-collecting chamber 162. Alternatively, in case that the inner pressure of the target equipment which is in communication with the outlet structure 19 is higher than the ambient air pressure, which means the gas pressure of the inner space of the target equipment is greater than the gas pressure of the input side, the gas-releasing operation may be performed. Under this circumstance, the gas is transferred from the outlet structure 19 to the second outlet chamber 184 through the outlet perforation 182. Consequently, the volume of the second outlet chamber 184 is expanded, and the flexible valve film 17 corresponding to the second outlet chamber 184 is subjected to the upward curvy deformation. In addition, the valve film 17 is in close contact with the gas collecting plate 16. Consequently, the valve opening 170 of the valve film 17 is closed by the gas collecting plate 16. Moreover, the gas collecting plate 16 has the raised structure 167 corresponding to the first outlet chamber 166. Due to the arrangement of the raised structure 167, the flexible valve film 17 can be bent upwardly more quickly. Moreover, the raised structure 167 can provide a pre-force to achieve a good sealing effect of the valve opening 170. Since the valve opening 170 of the valve film 17 is contacted with and closed by the raised structure 167, the gas in the second outlet chamber 184 will not be reversely returned to the first outlet chamber 166. Consequently, the efficacy of avoiding gas leakage is enhanced. Moreover, since the gas in the second outlet chamber 184 is transferred to the second pressure-releasing chamber 183 through the communication channel 185, the volume of the second pressure-releasing chamber 183 is expanded. Consequently, the valve film 17 corresponding to the second pressure-releasing chamber 183 is also subjected to the upward curvy deformation. Since the valve film 17 is no longer in contact with the first end of the pressure-releasing perforation 181, the pressure-releasing perforation 181 is opened. Under this circumstance, the gas in the second pressure-releasing chamber 183 is outputted through the pressure-releasing perforation 181. Consequently, the pressure of the gas is released. Similarly, due to the convex structure 181a beside the pressure-releasing perforation 181 or the position-limiting structure 188 within the second pressure-releasing chamber 183, the flexible valve film 17 can be subjected to the upward curvy deformation more quickly. Consequently, the pressure-releasing perforation 181 can be quickly opened. After the gas-releasing operation in one direction is performed, the gas within the inner space of the target equipment which is in communication with the outlet structure 19 is partially or completely exited to the surrounding. Under this circumstance, the gas pressure of the target equipment is reduced.

Figure 6A:
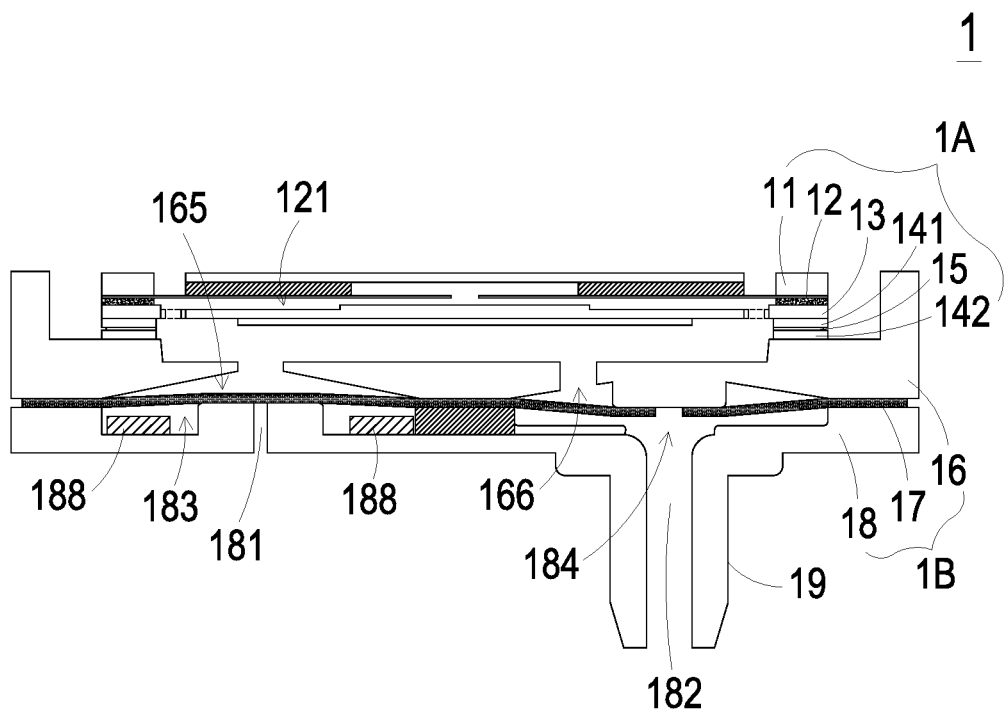
FIGS. 6A to 6E schematically illustrate a gas-collecting operation of the miniature pneumatic device of FIG. 1A.

FIGS. 6A to 6E schematically illustrate the gas-collecting actions of the miniature pneumatic device of FIG. 2A. Please refer to FIGS. 1A, 2A and 6A to 6E. As shown in FIG. 6A, the miniature pneumatic device 1 comprises the miniature fluid control device 1A and the miniature valve device 1B. As mentioned above, the gas inlet plate 11, the resonance plate 12, the piezoelectric actuator 13, the first insulation plate 141, the conducting plate 15, the second insulation plate 142 and the gas collecting plate 16 of the miniature fluid control device 1A are stacked on each other sequentially. There is a gap g0 between the resonance plate 12 and the piezoelectric actuator 13. Moreover, the first chamber 121 is formed between the resonance plate 12 and the piezoelectric actuator 13. The valve film 17 and the gas outlet plate 18 of the miniature valve device 1B are stacked on each other and disposed under the gas collecting plate 16 of the miniature fluid control device 1A. The gas-collecting chamber 162 is arranged between the gas collecting plate 16 and the piezoelectric actuator 13. The first pressure-releasing chamber 165 and the first outlet chamber 166 are formed in the second surface 161 of the gas collecting plate 16. The second pressure-releasing chamber 183 and the second outlet chamber 184 are formed in the first surface 180 of the gas outlet plate 18. In an embodiment, the operating frequency of the miniature pneumatic device 1 is in the range between 27 kHz and 29.5 kHz, and the operating voltage of the miniature pneumatic device 1 is in the range between ±10V and ±16V. Moreover, due to the arrangements of the plural pressure chambers, the actuation of the piezoelectric actuator 13 and the vibration of the plate 12 and the valve film 17, the gas can be transferred downwardly.

Figure 6B:
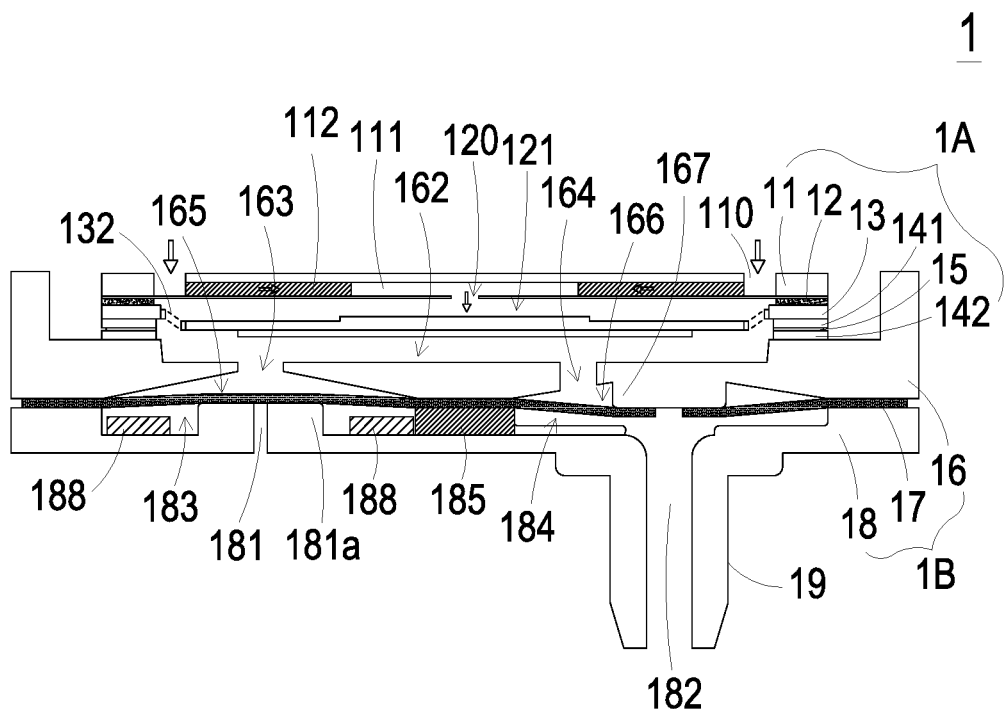

As shown in FIG. 6B, the piezoelectric actuator 13 of the miniature fluid control device 1A is vibrated downwardly in response to the applied voltage. Consequently, the gas is fed into the miniature fluid control device 1A through the at least one inlet 110 of the gas inlet plate 11. The gas is sequentially converged to the circular cavity 111 through the at least one convergence channel 112 of the gas inlet plate 11, transferred through the central aperture 120 of the resonance plate 12, and introduced downwardly into the first chamber 121.

Figure 6C:
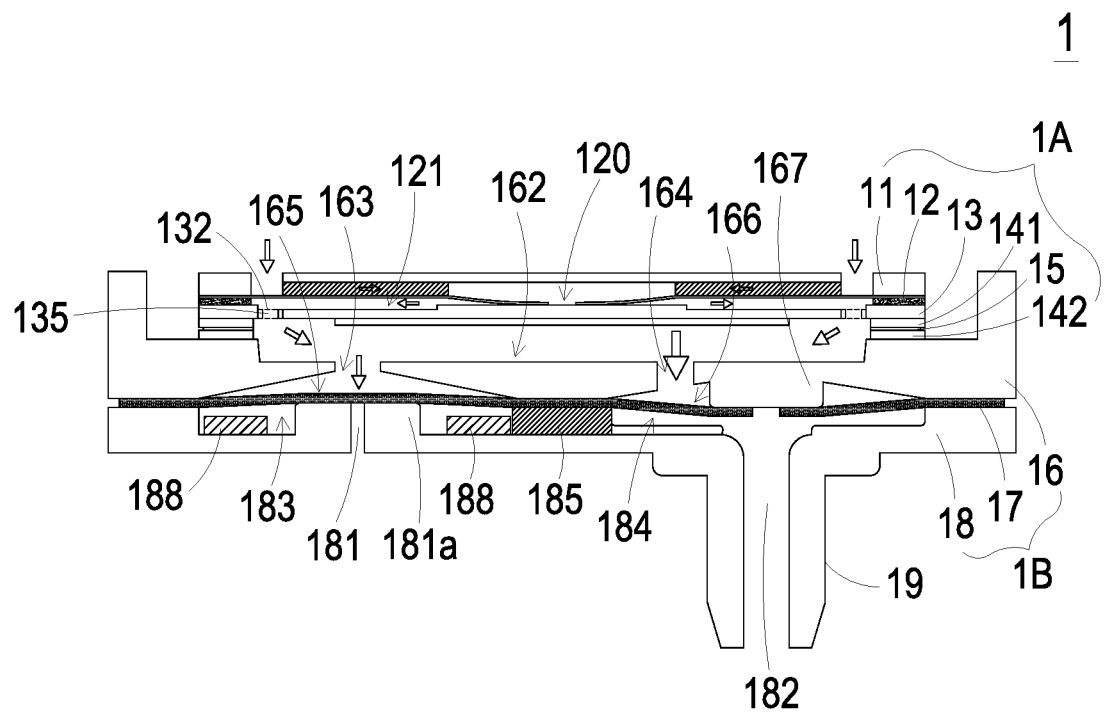

As the piezoelectric actuator 13 is actuated, the resonance of the resonance plate 12 occurs. Consequently, the resonance plate 12 is also vibrated along the vertical direction in the reciprocating manner. As shown in FIG. 6C, the resonance plate 12 is vibrated downwardly and contacted with the cylindrical bulge 130c of the suspension plate 130 of the piezoelectric actuator 13. Due to the deformation of the resonance plate 12, the volume of the chamber corresponding to the circular cavity 111 of the gas inlet plate 11 is expanded but the volume of the first chamber 121 is shrunken. Under this circumstance, the gas is pushed toward peripheral regions of the first chamber 121. Consequently, the gas is transferred downwardly through the vacant space 135 of the piezoelectric actuator 13. Then, the gas is transferred to the gas-collecting chamber 162 between the miniature fluid control device 1A and the miniature valve device 1B. After that, the gas is transferred downwardly to the first pressure-releasing chamber 165 and the first outlet chamber 166 through the first perforation 163 and the second perforation 164, which are in communication with the gas-collecting chamber 162. Consequently, when the resonance plate 12 is vibrated along the vertical direction in the reciprocating manner, the gap g0 between the resonance plate 12 and the piezoelectric actuator 13 is helpful to increase the amplitude of the resonance plate 12. That is, due to the gap g0 between the resonance plate 12 and the piezoelectric actuator 13, the amplitude of the resonance plate 12 is increased when the resonance occurs.

Figure 6D:
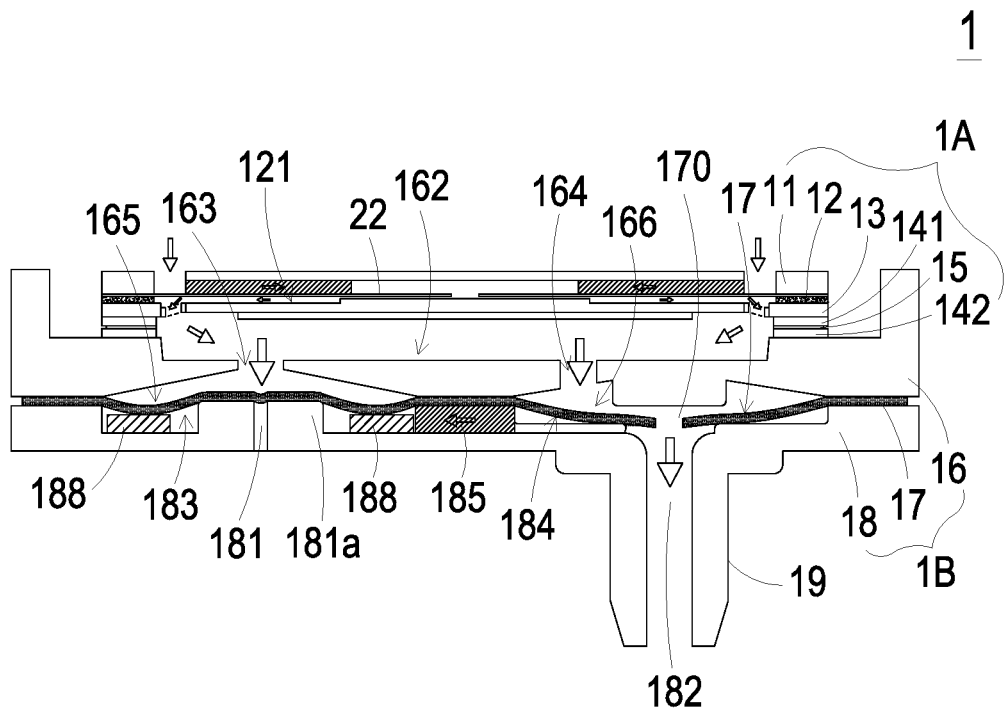

As shown in FIG. 6D, the resonance plate 12 of the miniature fluid control device 1A is returned to its original position, and the piezoelectric actuator 13 is vibrated upwardly in response to the applied voltage. Consequently, the volume of the first chamber 121 is also shrunken, and the gas is continuously pushed toward peripheral regions of the first chamber 121. Moreover, the gas is continuously transferred to the gas-collecting chamber 162, the first pressure-releasing chamber 165 and the first outlet chamber 166 through the vacant space 135 of the piezoelectric actuator 13. Consequently, the pressure in the first pressure-releasing chamber 165 and the first outlet chamber 166 will be gradually increased. In response to the increased gas pressure, the flexible valve film 17 is subjected to the downward curvy deformation. Consequently, the valve film 17 corresponding to the second pressure-releasing chamber 183 is moved downwardly and contacted with the convex structure 181a corresponding to the first end of the pressure-releasing perforation 181. Under this circumstance, the pressure-releasing perforation 181 of the gas outlet plate 18 is closed. In the second outlet chamber 184, the valve opening 170 of the valve film 17 corresponding to the outlet perforation 182 is opened downwardly. Then, the gas within the second outlet chamber 184 is transferred downwardly to the outlet structure 19 through the outlet perforation 182 and then transferred to the inner space of the target equipment which is in communication with the outlet structure 19. Consequently, the inner space of the target equipment is pressurized, and the purpose of collecting the gas pressure is achieved.

Figure 6E:
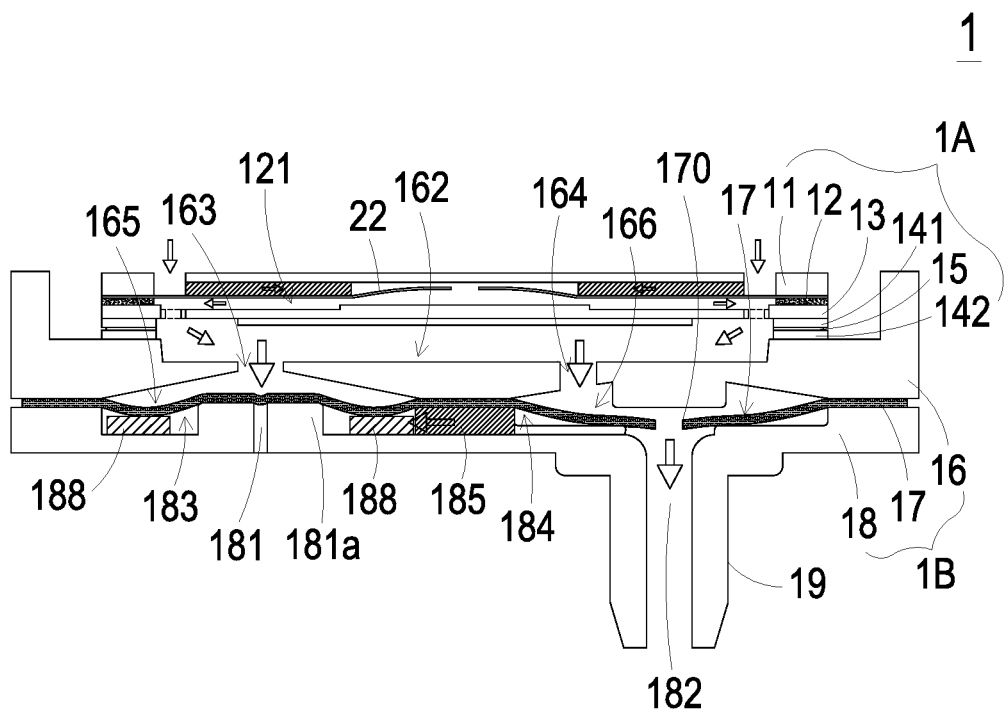

Then, as shown in FIG. 6E, the resonance plate 12 of the miniature fluid control device 1A is vibrated upwardly. Under this circumstance, the gas in the circular cavity 111 of the gas inlet plate 11 is transferred to the first chamber 121 through the central aperture 120 of the resonance plate 12, and then the gas is transferred downwardly to the gas collecting plate 16 through the vacant space 135 of the piezoelectric actuator 13. As the gas pressure is continuously increased along the downward direction, the gas is continuously transferred to the gas-collecting chamber 162, the second perforation 164, the first outlet chamber 166, the second outlet chamber 184 and the outlet perforation 182 and then transferred to the target equipment which is in communication with the outlet structure 19. Such pressure-collecting operation may be but not limited to be triggered by the pressure difference between the ambient pressure of the input side and the gas pressure of the inner space of the target equipment.

Figure 7:
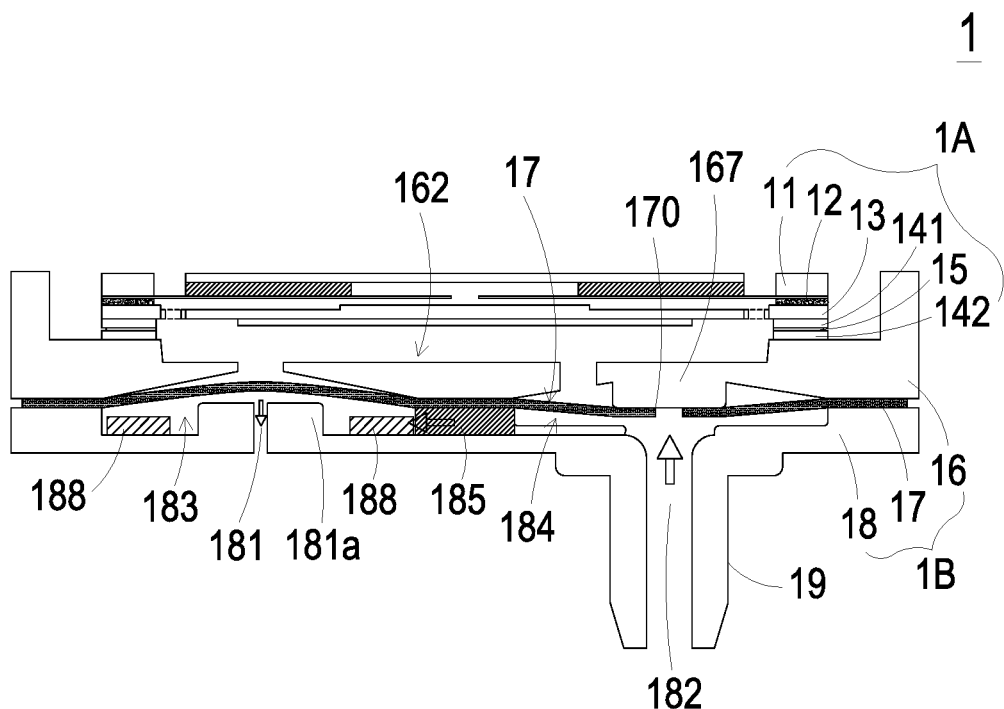
FIG. 7 schematically illustrate the gas-releasing actions or the pressure-reducing actions of the miniature pneumatic device of FIG. 1A.

FIG. 7 schematically illustrate the gas-releasing actions or the pressure-reducing actions of the miniature pneumatic device of FIG. 1A. In case that the inner pressure of the equipment which is in communication with the outlet structure 19 is higher than the ambient air pressure of the input side, the gas-releasing operation (or a pressure-reducing operation) may be performed. As mentioned above, the user may adjust the amount of the gas to be fed into the miniature fluid control device 1A, so that the gas is no longer transferred to the gas-collecting chamber 162. Under this circumstance, the gas is transferred from the outlet structure 19 to the second outlet chamber 184 through the outlet perforation 182. Consequently, the volume of the second outlet chamber 184 is expanded, and the flexible valve film 17 corresponding to the second outlet chamber 184 is bent upwardly. In addition, the valve film 17 is in close contact with the raised structure 167 corresponding to the first outlet chamber 166. Since the valve opening 170 of the valve film 17 is closed by the raised structure 167, the gas in the second outlet chamber 184 will not be reversely returned to the first outlet chamber 166. Moreover, the gas in the second outlet chamber 184 is transferred to the second pressure-releasing chamber 183 through the communication channel 185, and then the gas in the second pressure-releasing chamber 183 is transferred to the pressure-releasing perforation 181. Under this circumstance, the gas-releasing operation is performed. After the gas-releasing operation of the miniature valve device 1B in one direction is performed, the gas within the inner space of the target equipment which is in communication with the outlet structure 19 is partially or completely exited to the surrounding. Under this circumstance, the inner pressure of the equipment is reduced.

From the above descriptions, the present invention provides the miniature fluid control device capable of transporting gas and for use with the miniature pneumatic device. The miniature pneumatic device further comprises the miniature valve device. In the miniature fluid control device, the ratio of the second diameter of the cylindrical bulge of the suspension plate to the first diameter of the circular cavity of the gas inlet plate is set in a specified range. Consequently, the gas pressure of the gas transported by the miniature fluid control device is in an optimum range, which assuring the efficiency of gas transmission.

Moreover, the piezoelectric actuator of the miniature fluid control device generates a pressure gradient in the fluid channels and the gas-collecting chamber of the miniature fluid control device so as to facilitate the external gas to be fed into the miniature fluid control device through the inlet and flow at a high speed. Furthermore, due to the one-way valve film of the miniature valve device, the gas is transferred in one direction. Consequently, the pressure of the gas is accumulated to the target equipment that is connected with the outlet structure. For performing a gas-releasing operation (or a pressure-reducing operation), the user may adjust the amount of the gas to be fed into the miniature fluid control device, so that the gas is no longer transferred to the gas-collecting chamber. Under this circumstance, the gas is transferred from the outlet structure to the second outlet chamber of the miniature valve device, then transferred to the second pressure-releasing chamber through the communication channel, and finally exited from the pressure-releasing perforation. By the miniature pneumatic device of the present invention, the gas can be quickly transferred while achieving silent efficacy. Moreover, due to the special configurations, the miniature pneumatic device of the present invention has small volume and small thickness. Consequently, the miniature pneumatic device is portable and suitable to be applied to medical equipment or any other appropriate equipment. In other words, the miniature pneumatic device of the present invention has significant advantages that creating industrial values.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A miniature fluid control device for transporting gas, comprising:
   a gas inlet plate comprising a feeding surface and a coupling surface opposing to the feeding surface, wherein at least one inlet is formed in the feeding surface, at least one convergence channel and a circular cavity are concavely formed in the coupling surface, wherein the circular cavity has a first diameter, a first end of the convergence channel is in communication with the circular cavity, a second end of the convergence channel is in communication with the at least one inlet, and a convergence chamber is defined by the circular cavity, wherein after a gas is introduced into the at least one convergence channel through the at least one inlet, the gas is guided by the at least one convergence channel and converged to the convergence chamber;
   a resonance plate having a central aperture corresponding to the circular cavity of the gas inlet plate; and
   a piezoelectric actuator comprising a suspension plate, an outer frame, at least one bracket and a piezoelectric plate, wherein the suspension plate has a first surface and an opposing second surface, a cylindrical bulge is formed on the second surface of the suspension plate, the cylindrical bulge and the circular cavity are aligned with each other along a vertical direction, the cylindrical bulge has a second diameter, and there is a specified ratio of the second diameter to the first diameter that affects gas pressure of the transported gas, wherein the ratio of the second diameter to the first diameter is in a range between 0.95 and 1.15, wherein the outer frame is arranged around the suspension plate, the suspension plate and the outer frame are connected with each other through the at least one bracket, and the piezoelectric plate is attached on the first surface of the suspension plate,
   wherein the gas inlet plate, the resonance plate and the piezoelectric plate are stacked on each other sequentially, and a gap is formed between the resonance plate and the piezoelectric actuator to define a first chamber, wherein after the gas is fed into the at least one inlet of the gas inlet plate, the gas is converged to the circular cavity through the at least one convergence channel, transferred through the central aperture of the resonance plate, introduced into the first chamber, transferred downwardly through a vacant space between the at least one bracket of the piezoelectric actuator, and exited from the miniature fluid control device, by which the miniature fluid control device continuously outputs the transported gas.

2. The miniature fluid control device according to claim 1, wherein when the ratio of the second diameter to the first diameter is in the range between 0.95 and 1.15, the gas pressure of the transported gas is at least 380 mmHg.

3. The miniature fluid control device according to claim 1, wherein the ratio of the second diameter to the first diameter is in a range between 1.0 and 1.1.

4. The miniature fluid control device according to claim 3, wherein when the ratio of the second diameter to the first diameter is in a range between 1.0 and 1.1, the gas pressure of the transported gas is at least 410 mmHg.

5. The miniature fluid control device according to claim 1, wherein each of the suspension plate and the piezoelectric plate has a square shape.

6. The miniature fluid control device according to claim 5, wherein a length of the suspension plate is greater than a length of the piezoelectric plate.

7. The miniature fluid control device according to claim 6, wherein the length of the suspension plate is in a range between 8 mm and 9 mm.

8. The miniature fluid control device according to claim 7, wherein the length of the piezoelectric plate is in a range between 7.5 mm and 8.5 mm.

9. The miniature fluid control device according to claim 6, wherein the length of the suspension plate is 7.5 mm.

10. The miniature fluid control device according to claim 9, wherein the length of the piezoelectric plate is 7 mm.

11. The miniature fluid control device according to claim 1, wherein a thickness of the cylindrical bulge is in a range between 0.02 mm and 0.08 mm.

12. The miniature fluid control device according to claim 11, wherein the thickness of the cylindrical bulge is 0.03 mm.

13. The miniature fluid control device according to claim 1, wherein a depth of the circular cavity is in a range between 0.2 mm and 0.4 mm.

14. The miniature fluid control device according to claim 1, wherein a depth of the convergence chamber and a depth of the at least one convergence channel are equal.

15. The miniature fluid control device according to claim 1, wherein the miniature fluid control device further comprises at least one insulation plate and a conducting plate, wherein the at least one insulation plate and the conducting plate are stacked on each other and located under the piezoelectric actuator.

16. A miniature fluid control device for transporting gas, comprising:
   a gas inlet plate comprising a feeding surface and a coupling surface, wherein at least one inlet is formed in the feeding surface, at least one convergence channel and a circular cavity are concavely formed in the coupling surface, wherein the circular cavity has a first diameter;
   a resonance plate having a central aperture corresponding to the circular cavity of the gas inlet plate; and
   a piezoelectric actuator comprising a suspension plate and a piezoelectric plate, wherein the suspension plate has a first surface and an opposing second surface, a cylindrical bulge is formed on the second surface of the suspension plate, the cylindrical bulge and the circular cavity are aligned with each other along a vertical direction, the cylindrical bulge has a second diameter, and there is a specified ratio of the second diameter to the first diameter that affects gas pressure of the transported gas, wherein the ratio of the second diameter to the first diameter is in a range between 0.95 and 1.15,
   wherein the gas inlet plate, the resonance plate and the piezoelectric plate are stacked on each other sequentially to be positioned.

* * * * *